United States Patent [19]

Hurd et al.

[11] Patent Number: 4,795,541

[45] Date of Patent: Jan. 3, 1989

[54] METHOD AND APPARATUS FOR MOLDING THIN GEL SLABS HORIZONTALLY WITH INTEGRALLY MOLDED LARGE VOLUME SAMPLE WELLS

[75] Inventors: Stanley M. Hurd, Hamden; Richard E. Kouri, New Haven, both of Conn.

[73] Assignee: Bios Corporation, New Haven, Conn.

[21] Appl. No.: 51,761

[22] Filed: May 20, 1987

[51] Int. Cl.[4] .................... G01N 27/28; G01N 27/26
[52] U.S. Cl. ............................ 204/299 R; 204/182.8
[58] Field of Search ............. 204/299 R, 182.8, 182.9

[56] References Cited

U.S. PATENT DOCUMENTS

| | | | |
|---|---|---|---|
| 3,479,265 | 11/1969 | Elevitch | 204/299 R X |
| 3,766,047 | 10/1973 | Elevitch | 204/299 R |
| 3,767,560 | 10/1973 | Elevitch | 204/299 R |
| 3,888,759 | 6/1975 | Elson et al. | 204/299 R |
| 3,930,983 | 1/1975 | Sieber | 204/182.8 X |
| 3,964,992 | 6/1976 | Krotz | 204/299 R |
| 4,130,471 | 12/1978 | Grunbaum | 204/299 R X |
| 4,246,222 | 1/1981 | Monthony | 204/299 R X |
| 4,533,307 | 8/1985 | Ansorge | 204/299 R X |

Primary Examiner—John F. Niebling
Assistant Examiner—John S. Starsiak, Jr.
Attorney, Agent, or Firm—Bachman & LaPointe

[57] ABSTRACT

A method and apparatus is disclosed for molding thin gel slabs horizontally having deep, large volume sample wells molded integrally and in communication with the thin gel slab. The disclosure includes a method and apparatus for molding at least two contiguous thin gel slabs horizontally.

12 Claims, 3 Drawing Sheets

METHOD AND APPARATUS FOR MOLDING THIN GEL SLABS HORIZONTALLY WITH INTEGRALLY MOLDED LARGE VOLUME SAMPLE WELLS

BACKGROUND OF THE INVENTION

Electrophoresis is a process in which macromolecules are separated on the basis of their charge-to-mass ratios by forcing them to move through a gel by means of a voltage gradient applied across the gel. Those species having uniform charge-to-mass ratios, such as DNA and RNA, are sorted according to their sizes, since the smaller molecules are able to move through the gel matrix more rapidly.

There are two basic formats used routinely in apparatus for electrophoresis of DNA: vertical and horizontal units. The vertical units, in which the gels are cast between two vertical non-conductive plates, offer greater reproducibility because of the uniform gel configurations created by the plates. They also allow for the application of larger sample volumes due to the fact that the sample wells are cast in the same plane as the gels, while the wells in horizontal units are cast into the thickness of the gels. The horizontal units offer greater ease in casting the gels, and do not require the troublesome precautions against leaking associated with the vertical units.

The present device incorporates the advantages of the vertical unit with the ease of operation of the horizontal unit by the addition of a novel plate which forms an upper boundary on the surface of the gel slab. Other such top plates have been described for horizontal electrophoresis units (see, e.g., Elson, D., and Avital, S., U.S. Pat. No. 3,888,759), but they do not address the problems of restricted sample volumes. Their apparatus also requires a larger number of elements, making it relatively complicated to set up. In the present invention, the top plate serves not only to provide a smooth, uniform gel, it also provides a vertically oriented application well that allows for the same sample volumes normally associated with vertical apparatus. In addition, it is notably simpler in operation than that described by Elson and Avital.

There are several other advantages to the use of such a top plate, both in general and in respect to the use of the resultant gels in the subsequent blotting procedures. First, the uniform cross-section of the gel provides a more reproducible electrophoretic pattern. Second, the top plate serves as a thermal insulator so that when the agarose gels are cast, the rate of cooling is reduced, thus reducing convection as the gel sets. This also provides a more uniform gel. Third, gels only 0.15-0.3 mm thick can be cast reproducibly, and this allows for more rapid separation of DNA fragments and also more rapid transfer of these fragments during the subsequent blotting procedure. Fourth, the flat upper surface is desirable for the subsequent blotting procedure, in which a thin membrane is placed in contact with the gel surface.

The present invention also embodies a feature found previously only in vertical gel units: the ability to cast two-gel systems. These two-gel systems are used routinely in high-resolution procedures such as the well-known Laemmli technique (Laemmli, U. K., *Nature*, 1970). Such procedures offer the advantage of tighter, more concentrated bands in the electrophoresis gel, and hence a more rapid, higher resolution blot. The present invention uses a space-filling element or a blank in place of one portion of the top plate, causing the gel material to be excluded from a portion of the gel tray. After the gel has set, the space-filling element may be removed and another suitable gel material cast contiguously in the space so provided.

In the present device the tray in which the gels are cast performs an additional function. It is used to carry the gel from the electrophoresis unit to the blotting unit and the gel may be left on the tray throughout the blotting procedure. This greatly increases the ease with which the operator can handle the gels. It also allows for the use of much thinner gels, with the benefits common to such gels. In fact, this makes it possible to use thinner gels, and at lower gel concentrations, than is currently possible with either vertical or horizontal systems.

It is, therefore, an object of the current invention to provide a method and an apparatus for casting thin horizontal electrophoresis gels that shall have increased sample capacity.

It is another object of the present invention to provide a means of casting two-gel systems in a horizontal unit.

It is another object of the current invention to provide horizontal gels of uniform, well-defined cross sections and smooth, flat surfaces.

It is a further object of the present invention to provide a means by which gels of lower concentration and having thinner cross sections than is possible with present techniques may be cast, electrophoresed, and blotted conveniently.

A further object of the present invention is the provision of a novel method and apparatus for molding a thin gel slab and a contiguous high volume sample well simultaneously.

Other features and advantages of the present invention will become more apparent from an examination of the following specification when read in conjunction with the appended drawings, in which;

DESCRIPTION OF PREFERRED EMBODIMENTS

Figure 3:
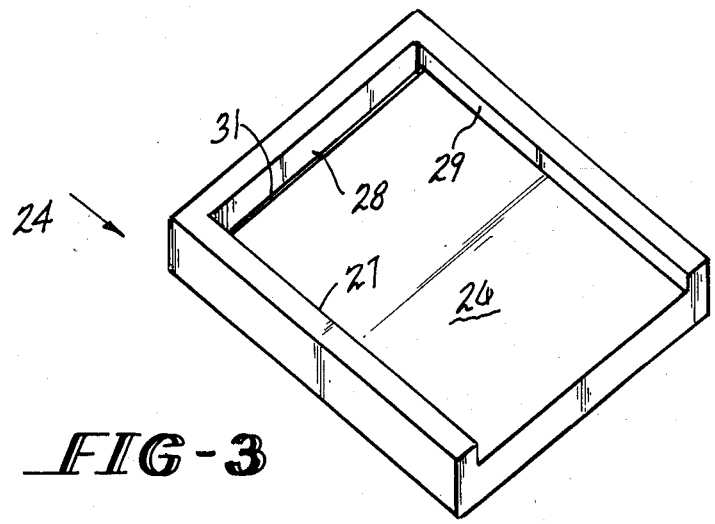
FIG. 3 is a perspective view of inside of the top mold tray.
Figure 1:
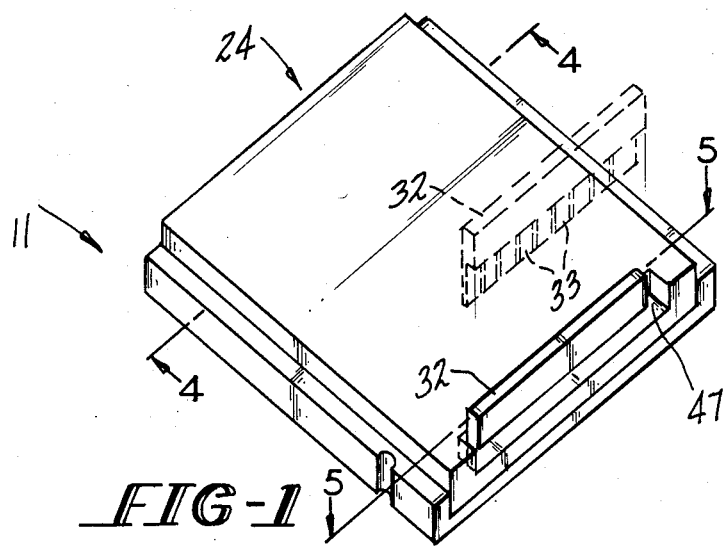
FIG. 1 is a perspective view of the assembled gel mold with the well template shown in the molding position in solid lines and poised for insertion in dashed lines.
Figure 2:
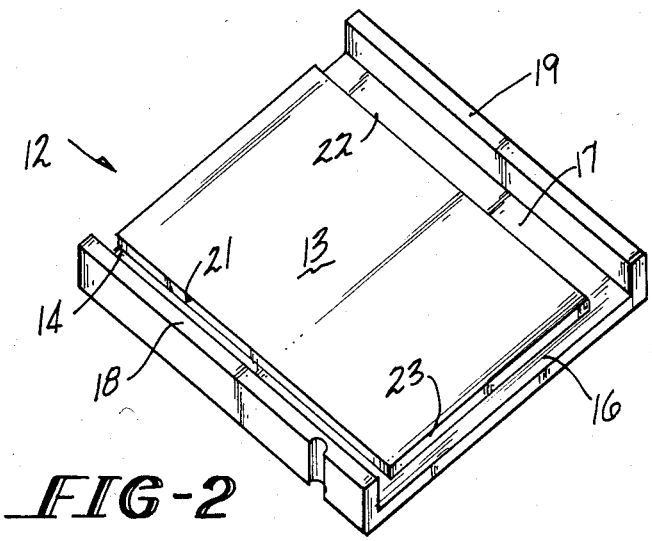
FIG. 2 is a perspective view of the bottom mold tray.

Referring to FIGS. 1, 2 and 3 the reference numeral 11 designates an assembled gel mold for molding thin gel slabs ranging from 0.1 mm. to 3.0 mm. in thickness.

The assembly includes a bottom tray 12 having a planar platform defining a first mold surface or mold plate 13 surrounded by a base plane defined by flats 14, 16 and 17.

The bottom tray includes side walls 18 and 19 which cooperate with the sides 21, 22 and 23 of the platform to key or lock the mold assembly in proper position in a manner which will be more apparent as the specification proceeds.

Top tray 24 includes a second mold surface or mold plate 26 bounded by a skirt comprising skirt elements 27, 28 and 29. As is most apparent in FIGS. 1, 3 and 6, the top tray 24 is formed with a through slot 31 for receiving a template or mold core 32 having a plurality of tines 33—33 for molding deep sample wells 20 which communicate with and form extensions of shallow sample wells 25 molded in a thin gel slab 30. The through slot includes sidewalls 10 and 15 defining vertical mold plates.

Figure 4:
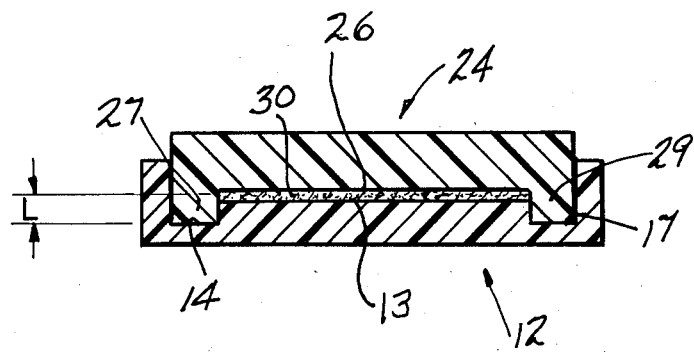
FIG. 4 is a vertical section through the assembled mold of FIG. 1 as observed in the direction of the arrows 4—4, showing a molded gel slab.

As is most apparent in FIG. 4 the skirt elements 27, 28 and 29 of top tray 24, in the assembled condition of the mold trays, bear upon the base plane flats 14, 16 and 17 and in cooperation with the elevation of platform 13 establish the thickness dimension of a molded gel slab.

Usually the elevation of the platform, defining the first mold surface 13, is fixed and the thickness dimension of the molded slab is changed by changing the length L of the skirt elements depending from the top tray.

That is, one top tray 24 is formed with a skirt dimension that will produce a slab of a predetermined thickness and another top tray of a different skirt dimension produces a correspondingly different slab thickness.

When it is desired to mold a thin gel slab in combination with a deep sample well the bottom tray 12 is disposed in a suitable container or receptacle (not shown). Liquid gel material is deposited upon the mold surface 13 and the top tray 24 is assembled in the manner shown in FIGS. 1 and 4. Sufficient gel material is supplied so that in addition to molding a thin slab 30 excess gel extrudes into the elongated slot 31 filling the slot to mold a vertical slab between slot sidewalls or mold plates 10 and 15.

Figure 5:
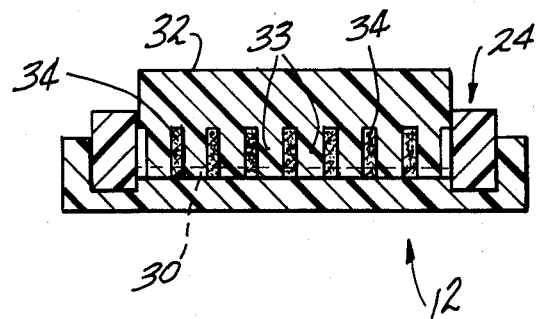
FIG. 5 is a vertical section through the assembled mold of FIG. 1 in the plane of the line 5—5 showing the mold template a molded slab and molded gel columns.

Next the template 32 is inserted into the gel filled slot and pressed "home" so that the tines 33—33 displace gel and bottom on the platform 13 (the first mold surface) as shown in FIG. 5.

Note that this occurrence creates shallow wells 25—25 (FIG. 6) in the gel slab 30 which are continuous with deep wells 20—20 formed by molded gel columns 34—34 and the internal side walls 10 and 15 of the slot 31. That is, the displacement of gel by the tines creates wells.

Figure 6:
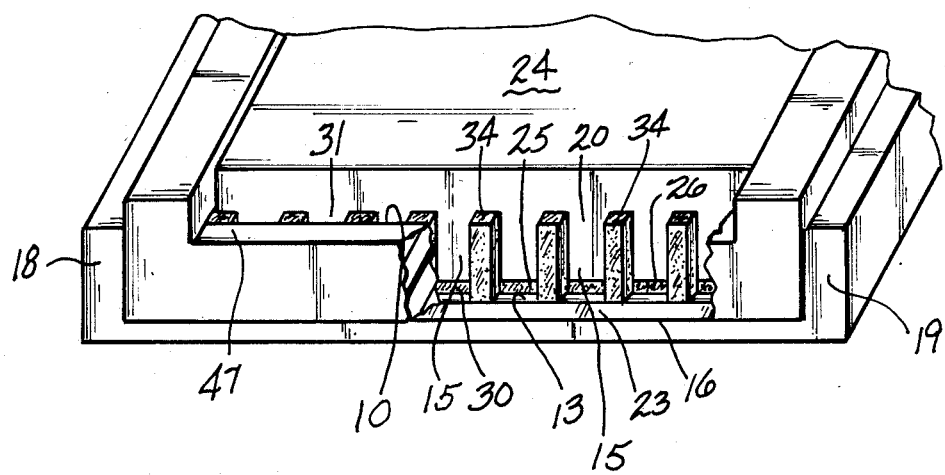
FIG. 6 is an enlarged view of a portion of the right end of FIG. 1 with parts broken away showing, with greater clarity, the sample wells molded integrally with the gel slab and with the template removed.

After the gel has "set" removal of the template 32 presents a sample well structure as shown in FIG. 6 in which a large volume sample well is available to complement a very small volume sample well in the thin gel slab.

Thus, in the practice of the principles of the present invention it is possible, using a template having tines of a given cross-sectional area, to mold large volume sample wells communicating with gel slabs ranging in thickness from 0.1 mm. to 3.0 mm. whose volume ranges from 5 to 100 times the volume of a well confined to the thin slab, per se.

Figure 7:
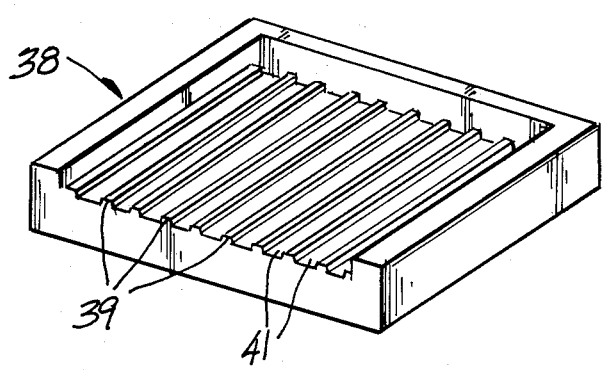
FIG. 7 shows the inside of an alternative top mold tray formed with lands and grooves; and, FIG. 8 shows a top mold tray comprised of a number of piece parts for molding separate but contiguous horizontal thin slabs.

FIG. 7 shows a modified top tray 38 having a plurality of lands 39 and grooves 41. This top tray is designed to mold a plurality of elongated gel slabs in the grooves 41. That is, when this top tray is assembled to the bottom tray 12 with an appropriate supply of gel compound, the lands 39 contact the mold surface 13 and the grooves mold a plurality of elongated individual thin gel slabs.

The grooves are formed in the top tray 38 so that the elongated molded gel slabs register with the tines 33 of the template to make certain that the deep sample wells formed by the template register with the slabs molded by the grooves.

Figure 8:
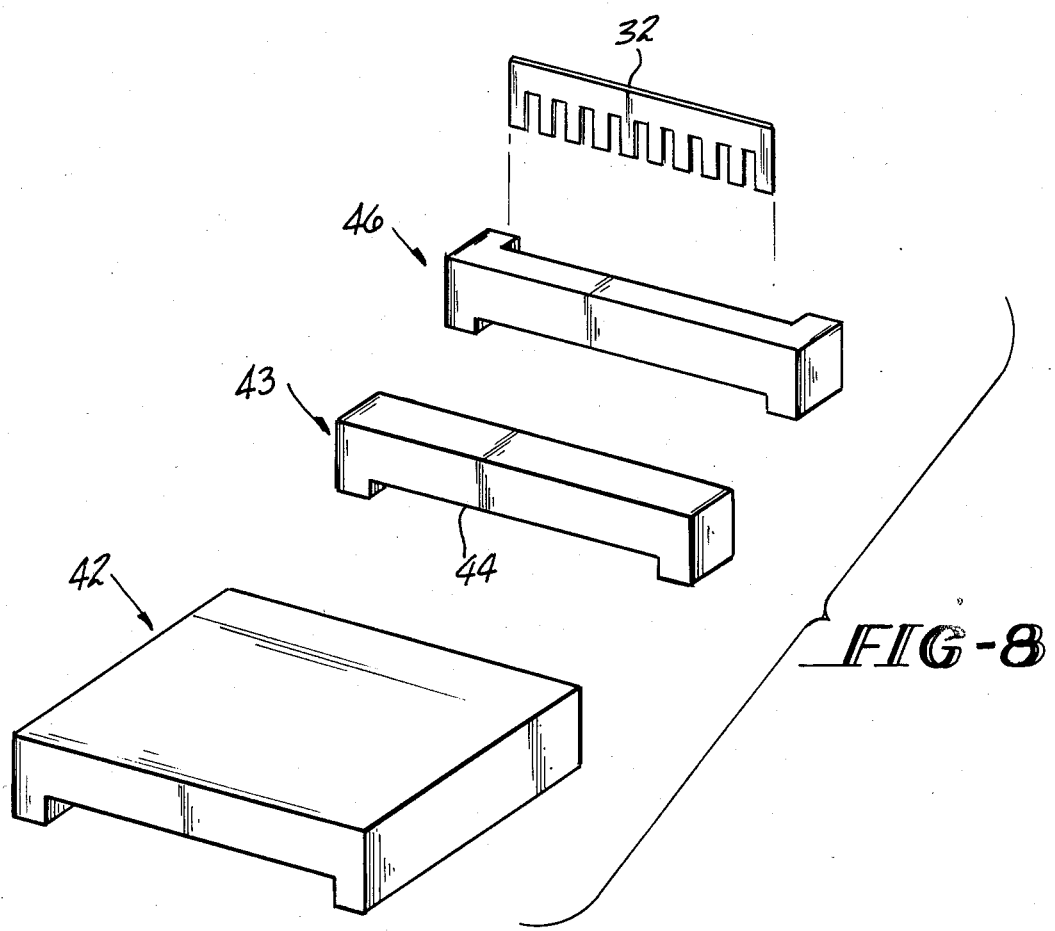

FIG. 8 illustrates a top mold tray in the form of a plurality of separable piece parts for molding at least two adjoining gel slabs. The top tray 42 is shorter than top tray 24 of FIGS. 1, 2 and 3 and is complemented by a blank piece part 43 whose underside 44 makes face to face contact with mold surface 13 (FIG. 2) to block gel seepage and to establish a small mold cavity (first cavity) defined by the size of the top tray 42. After the gel in the first mold cavity has set, the blank 43 is removed and replaced by an additional top tray piece part 46 including a template and template slot.

That is, a new or different gel material is supplied to that portion of the first mold surface 13 which is exposed and an additional mold cavity (second mold cavity) formed by top tray part 46 adjoining the first gel is operable to mold a second different gel following the procedure previously described.

Upon insertion of the template 32, sample wells are molded in the same fashion as described previously with respect to the wells shown and described with respect to FIGS. 5 and 6.

Referring to FIGS. 1 and 6, it is noted that it is desirable to provide a dam or weir in the top tray in the region of the elongated slot 31 to provide a fluid path for buffer liquid to flow into the mouths or top openings of the sample wells and thence down the well into the gel slabs.

That is, the right side (FIG. 1) of the top tray 24, for example, is provided with a cut out or step 47 defining a weir or dam over which buffer liquid flows prior to entering the respective sample wells.

The said fluid path establishes electrical communication between the sample wells and the voltage source used to drive the sample species into and through the gels.

Note further that while the slot 31 and the mating template 32 are shown in a generally vertically position it is entirely within the spirit and scope of the invention to cant the slot and the template at an angle to the horizontal.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A mold assembly for casting thin electrophoretic gel slabs in horizontal orientation comprising:
   a bottom tray means defining a first mold surface;

a top tray means having a second mold surface keyed to said bottom tray means;
a base plane surrounding a portion of said first mold surface;
skirt means on said top tray means engagable with said base plane for spacing said mold surfaces, the spacing of said mold surfaces ranging from 0.1 mm. to 3.0 mm.

2. The mold assembly of claim 1 in which the top tray means is formed with a through slot intersecting the space between said mold surfaces and a template means having at least one tine is operable to be received in said slot with said one tine bottoming on said first mold surface whereby said template means is operative to form sample wells when gel material is introduced into said slot and between said mold surfaces.

3. An apparatus for use in horizontal electrophoresis comprising a horizontal electrophoretic gel slab sandwiched between a pair of horizontal gel mold plates, at least one generally vertical gel column supported by one of said horizontal mold plates and connected to said horizontal gel slab;
said gel column being enclosed between vertical mold plates to define at least two sample wells;
one of said vertical mold plates defining a weir means facilitating overflow of liquid from a communicating buffer reservoir into said wells.

4. The apparatus of claim 3 including a plurality of spaced gel columns each supported by one of said horizontal mold plates and defining a vertical extension of said horizontal gel slab, said gel columns being enclosed between said vertical mold plates, said gel columns in combination with said vertical mold plates and said one of said horizontal mold plates defining a plurality of vertical sample wells each communicating with said horizontal gel slab.

5. The apparatus of claim 4 in which the horizontal gel slab has a thickness ranging from 0.1 mm. to 3.0 mm. and the volume of each said sample well of a given cross-sectional area ranges from 5 to 100 times the volume of a sample well of equivalent area limited to the thickness (height) of said horizontal gel slab.

6. The mold assembly of claim 2 in which the second mold surface is formed with a plurality of lands and grooves, said lands being in face to face contact with said first mold surface and said grooves being operable to mold individual elongated gel slabs, and said one tine of said template means being in register with one of said grooves so that when said gel material is introduced into said slot and into said one of said grooves said tine serves as a mold core to form a sample well contiguous with an elongated gel slab molded in said one of said grooves.

7. A horizontal electrophoresis apparatus comprising:
top and bottom mold trays,
said top tray having an opening,
a horizontal gel slab sandwiched between said mold trays,
said horizontal gel slab having at least two contiguous gel columns, and
said gel columns projecting into the opening in said top mold tray to define at least one sample well.

8. The apparatus of claim 7 in which the opening defines an elongated slot and the gel columns are received within the gel slab.

9. The apparatus of claim 8 in which the gel columns are disposed generally perpendicular to the gel slab.

10. The apparatus of claim 7 in which the horizontal gel slab is connected to at least three gel columns, said gel columns projecting into the opening in said top tray to define at least two sample wells.

11. The apparatus of claim 7 in which the sample well has a sidewall structure comprising:
portions of said top tray in combination with said gel slab and said gel columns.

12. The apparatus of claim 8 in which the slot is positioned at a margin of said gel slab.

* * * * *

UNITED STATES PATENT AND TRADEMARK OFFICE
CERTIFICATE OF CORRECTION

PATENT NO. : 4,795,541

DATED : January 3, 1989

INVENTOR(S) : STANLEY M. HURD ET AL.

It is certified that error appears in the above-identified patent and that said Letters Patent is hereby corrected as shown below:

Column 5, claim 1, line 2, after "means" insert --, said top tray means defines at least two separate pieces parts dividing said second mold surface into a plurality of mold surfaces, each mold surface of said plurality of mold surfaces cooperating with said first mold surface to form separate mold cavities thereby facilitating molding at least two individual but contiguous gel slabs in horizontal orientation and in sequential fashion--.

Column 6, claim 8, line 26, delete "gel slabs" and insert --elongated slot--.

Signed and Sealed this

Thirteenth Day of June, 1989

Attest:

DONALD J. QUIGG

*Attesting Officer*      *Commissioner of Patents and Trademarks*